(12) United States Patent
Ghosh et al.

(10) Patent No.: US 9,062,057 B2
(45) Date of Patent: Jun. 23, 2015

(54) CCR5 ANTAGONISTS FOR TREATING HIV

(75) Inventors: Arun K. Ghosh, West Lafayette, IN (US); Hiroaki Mitsuya, Kumamoto (JP); Venkateswararao Kalapala, West Lafayette, IN (US); Jianfeng Li, New York, NY (US)

(73) Assignees: Purdue Research Foundation, West Lafayette, IN (US); Hiroaki Mitsuya, Kumamoto (JP)

( * ) Notice: Subject to any disclaimer, the term of this patent is extended or adjusted under 35 U.S.C. 154(b) by 198 days.

(21) Appl. No.: 13/635,749

(22) PCT Filed: Mar. 18, 2011

(86) PCT No.: PCT/US2011/029004
§ 371 (c)(1),
(2), (4) Date: Feb. 1, 2013

(87) PCT Pub. No.: WO2011/116287
PCT Pub. Date: Sep. 22, 2011

(65) Prior Publication Data
US 2014/0221420 A1 Aug. 7, 2014

Related U.S. Application Data

(60) Provisional application No. 61/315,669, filed on Mar. 19, 2010.

(51) Int. Cl.
- *C07D 471/04* (2006.01)
- *C07D 487/04* (2006.01)
- *C07D 493/04* (2006.01)
- *C07D 451/04* (2006.01)
- *C07D 221/20* (2006.01)
- *C07D 519/00* (2006.01)

(52) U.S. Cl.
CPC ............ *C07D 487/04* (2013.01); *C07D 221/20* (2013.01); *C07D 451/04* (2013.01); *C07D 471/04* (2013.01); *C07D 519/00* (2013.01); *C07D 493/04* (2013.01)

(58) Field of Classification Search
None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,630,200 A | 12/1971 | Higuchi | |
| 3,847,770 A | 11/1974 | Radlowe et al. | |
| 3,916,899 A | 11/1975 | Theeuwes et al. | |
| 4,008,719 A | 2/1977 | Theeuwes | |
| 4,687,610 A | 8/1987 | Vassilatos | |
| 4,769,027 A | 9/1988 | Baker | |
| 5,059,595 A | 10/1991 | Grazie | |
| 5,073,543 A | 12/1991 | Marshall | |
| 5,120,548 A | 6/1992 | McClelland et al. | |
| 5,354,566 A | 10/1994 | Addesso et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 5,808,065 A | 9/1998 | Ishida et al. | |
| 5,962,462 A | 10/1999 | Mills et al. | |
| 6,013,644 A | 1/2000 | Mills et al. | |
| 6,013,652 A | 1/2000 | Maccoss et al. | |
| 6,136,827 A | 10/2000 | Caldwell et al. | |
| 6,140,349 A | 10/2000 | Caldwell et al. | |
| 2008/0070902 A1 | 3/2008 | Kimura et al. | |

FOREIGN PATENT DOCUMENTS

| | | |
|---|---|---|
| EP | 2547203 A1 | 1/2013 |
| JP | 2013522321 A | 6/2013 |
| WO | WO 2011/011652 | 1/2011 |
| WO | WO-2011011652 A1 | 1/2011 |
| WO | WO-2011116287 A1 | 9/2011 |

OTHER PUBLICATIONS

Supplementary European Search Report for European Patent Application No. 11757061 dated Nov. 25, 2013, 3 pages.
"European Application Serial No. 11757061.4, Extended European Search Report mailed Nov. 25, 2013", 5 pgs.
"European Application Serial No. 11757061.4, Office Action mailed Oct. 26, 2012", 2 pgs.
"European Application Serial No. 11757061.4, Response filed May 2, 2013 to Office Action mailed Oct. 26, 2012", 8 pgs.
"International Application Serial No. PCT/US2011/029004, International Preliminary Report on Patentability mailed May 23, 2013", 6 pgs.
PCT International Search Report and Written Opinion for PCT/US2011/029004, mailed May 3, 2011.
Shah, S. K., et al., "Synthesis and evaluation of CCR5 antagonists containing modified 4-piperidinyl-2-phenyl-1-(phenylsulfonylamino)-butane," Bioorganic & Medicinal Chemistry Letters, 15, 2005, 977-982.
Stupple, P. A., et al., "An Imidazopiperidine Series of CCR5 Antagonists for the Treatment of HIV: The Discovery of N-{(1S)-1-(3-Fluorophenyl)-3-[(3-endo)-3-(5-isobutyryl-2-methyl-4,5,6,7-tetrahydro-1H-imidazo[4,5-c]pyridin-1-yl)-8-azabicyclo[3.2.1]oct-8-yl]propyl}acetamide (PF-232798)," J. Med. Chem, 54, 2011, 67-77.

*Primary Examiner* — Timothy R Rozof
(74) *Attorney, Agent, or Firm* — Schwegman Lundberg & Woessner, P.A.

(57) ABSTRACT

Compounds that modulate the CCR5 chemokine receptor, pharmaceutical compositions containing them, and uses therefor in the treatment of HIV and related diseases are described.

13 Claims, No Drawings

CCR5 ANTAGONISTS FOR TREATING HIV

CROSS-REFERENCE TO RELATED APPLICATIONS

This application is a national stage entry under 35 USC §371(b) of International Application No. PCT/US2011/029004, filed Mar. 18, 2011, which claims priority under 35 U.S.C §119(e) to U.S. Provisional Application Ser. No. 61/315,669, filed on Mar. 19, 2010, the disclosures of which are incorporated herein by reference.

TECHNICAL FIELD

The invention described herein pertains to compounds that modulate the CCR5 chemokine receptor, pharmaceutical compositions containing them, and uses therefor in the treatment of HIV and related diseases.

BACKGROUND AND SUMMARY OF THE INVENTION

Highly active anti-retroviral therapy (HAART) has traditionally consisted of combination therapy with nucleoside reverse transcriptase inhibitors (NRTI), non-nucleoside reverse transcriptase inhibitors (NNRTI) and protease inhibitors (PI). These compounds inhibit biochemical processes required for viral replication. In compliant drug-naive patients, HAART is effective in reducing mortality and progression of HIV-1 to AIDS. While HAART has dramatically altered the prognosis for HIV infected persons, there remain many drawbacks to the current therapy including highly complex dosing regimes and side effects which can be very severe. Moreover, these multidrug therapies do not eliminate HIV-1 and long-term treatment usually results in multidrug resistance, thus limiting their utility in long term therapy. Development of new drug therapies to provide better HIV-1 treatment remains a priority.

The chemokines, a subset of the cytokine family of soluble immune modulators, are a large family of pro-inflammatory peptides that exert their pharmacological effect through G-protein-coupled receptors. The chemokines are leukocyte chemotactic proteins capable of attracting leukocytes to various tissues, which is an essential response to inflammation and infection. Human chemokines include approximately 50 structurally homologous small proteins comprising 50-120 amino acids. The CCR5 receptor is one member of this family.

Chemokine receptors have a 7 transmembrane structure and couple to a G-protein for signal transduction within a cell when bound to an agonist. Human CCR5 is composed of 352 amino acids with an intra-cellular C-terminus containing structural motifs for G-protein association and ligand-dependent signaling. The extracellular N-terminal domain contributes to high-affinity chemokine binding and interactions with the gp120 HIV protein. The natural ligands for the CCR5 are the macrophage inflammatory proteins (MIP) designated MIP-1a and MIP-1b and RANTES. The binding site for RANTES (Regulated upon Activation and is Normal T-cell Expressed and Secreted) has been shown to be on the N-terminal domain and HIV gp120 has been suggested to interact initially with the N-terminal domain and also with the ECL2 (extra-cellular loop 2).

Modulators of the CCR5 receptor may be useful in the treatment of infection by HIV-1 and genetically related retroviruses. HIV-1 infects cells of the monocyte-macrophage lineage and helper T-cell lymphocytes by exploiting a high affinity interaction of the viral enveloped glycoprotein (Env) with the CD4 antigen. The CD4 antigen appears to be a necessary, but not sufficient requirement for cell entry and at least one other surface protein is required to infect the cells. Two chemokine receptors, either the CCR5 (M-trophic strains) receptor or the CXCR4 (T-trophic strains) receptor are required, along with CD4, for infection of cells by the human immunodeficiency virus (HIV). The central role of CCR5 in the pathogenesis of HIV was inferred by epidemiological identification of powerful disease modifying effects of the naturally occurring null allele CCR5 Δ32. The Δ32 mutation has a 32-base pair deletion in the CCR5 gene resulting in a truncated protein designated Δ32. Relative to the general population, Δ32/Δ32 homozygotes are significantly common in exposed/uninfected individuals suggesting the role of CCR5 in HIV cell entry.

The HIV-1 envelope protein is comprised of two subunits: gp120, the surface subunit and gp41, the transmembrane subunit. The two subunits are non-covalently associated and form homotrimers which compose the HIV envelope. Each gp41 subunit contains two helical heptad repeat regions, HR1 and HR2 and a hydrophobic fusion region on the C-terminus.

Viral fusion and cell entry is a complex multi-step process and each step affords the potential for therapeutic intervention. The CD4 binding site on the gp120 of HIV appears to first interact with the CD4 molecule on the cell surface inducing a conformation change in gp120 which creates or exposes a cryptic CCR5 (or CXCR4) binding site, and undergoes conformational changes which permits binding of gp120 to the CCR5 and/or CXCR4 cell-surface receptor. The bivalent interaction brings the virus membrane into close proximity with the target cell membrane and the hydrophobic fusion region can insert into the target cell membrane. A conformation change in gp41 creates a contact between the outer leaflet of the target cell membrane and the viral membrane which produces a fusion pore whereby viral core containing genomic RNA enters the cytoplasm. Without being bound by theory, it is believed that the conformational changes induced by these steps expose additional targets for chemotherapeutic intervention. Each of these steps may afford an opportunity for therapeutic intervention in preventing or slowing HIV infection.

The therapeutic blockade of CCR5 as a treatment for HIV/AIDS has been demonstrated by the introduction of the CCR5 antagonist maraviroc. Clinical results suggested that maraviroc is potent and tolerable in patients with resistance to multiple antiretroviral medications. Therefore, there is a need for new and more effective CCR5 antagonists with minimal side effects and greater selectivity.

It has been unexpectedly discovered that the compounds described herein are potent modulators of CCR5 and effective antiretrovirals. Without being bound by theory, it is believed that the antiretroviral activity of these compounds results from the compounds ability to act as CCR5 antagonists.

In one illustrative embodiment of the invention, compounds of the formula

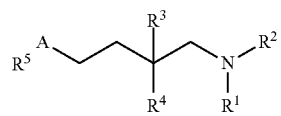

or a pharmaceutically acceptable salt thereof, wherein:

A is a conformationally constrained pyrrolidine or piperidine; or a bicyclic pyrrolidine or piperidine;

$R^1$ is hydrogen or optionally substituted alkyl;
$R^2$ is acyl or sulfonyl;
$R^3$ is hydrogen or optionally substituted alkyl;
$R^4$ is optionally substituted aryl; and
$R^5$ is hydrogen, optionally substituted heteroaryl, acyl, acylamino, sulfonyl, or sulfonylamino are described.

In another embodiment, pharmaceutical compositions are described which comprise one or more of the compounds described herein.

In another illustrative embodiment, a method is described for treating a patient in need of relief from HIV infection, the method comprising the step of administering to the patient a therapeutically effective amount of a compound or a composition described herein.

DETAILED DESCRIPTION

In one embodiment, a compound of the formula

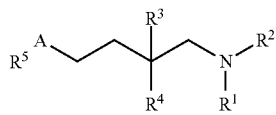

or a pharmaceutically acceptable salt thereof, wherein:
A is a conformationally constrained pyrrolidine or piperidine; including a bicyclic pyrrolidine or piperidine;
$R^1$ is hydrogen or optionally substituted alkyl;
$R^2$ is acyl or sulfonyl;
$R^3$ is hydrogen or optionally substituted alkyl;
$R^4$ is optionally substituted aryl; and
$R^5$ is hydrogen, optionally substituted heteroaryl, acyl, acylamino, sulfonyl, or sulfonylamino is described.

In another embodiment, herein described is the compound of the preceding embodiment wherein the compound has the following absolute stereochemistry

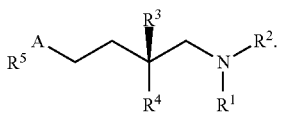

In another embodiment, the compound of any one of the preceding embodiments wherein A is a pyrrolopiperidine is described.

In another embodiment, the compound of any one of the preceding embodiments wherein A is a pyrrolopyrrolidine is described.

In another embodiment, the compound of any one of the preceding embodiments wherein A is a piperidinopiperidine is described.

In another embodiment, the compound of any one of the preceding embodiments wherein A is a divalent bridged bicyclic radical is described.

In another embodiment, the compound of any one of the preceding embodiments wherein A is an azabicyclooctane is described.

In another embodiment, the compound of any one of the preceding embodiments wherein A is selected from the following

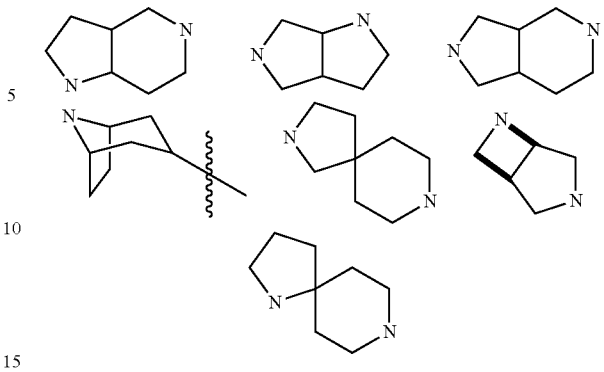

each of which is optionally substituted, is described.

In another embodiment, the compound of any one of the preceding embodiments wherein A is selected from the following

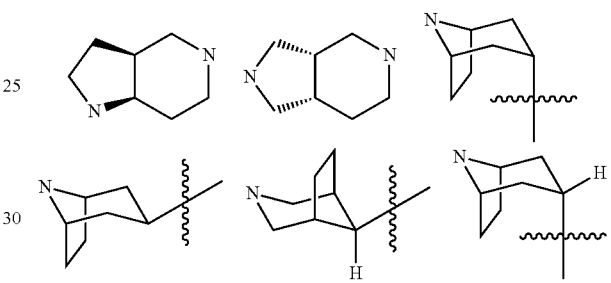

each of which is optionally substituted, is described. It is to be understood that the foregoing refer to both relative and absolute stereochemistry.

In another embodiment, the compound of any one of the preceding embodiments wherein A is

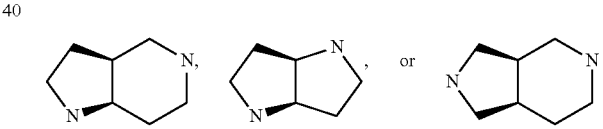

each of which is optionally substituted, is described. It is to be understood that the foregoing refer to both relative and absolute stereochemistry.

In another embodiment, herein described is the compound of any one of the preceding embodiments wherein the compound has the following stereochemistry

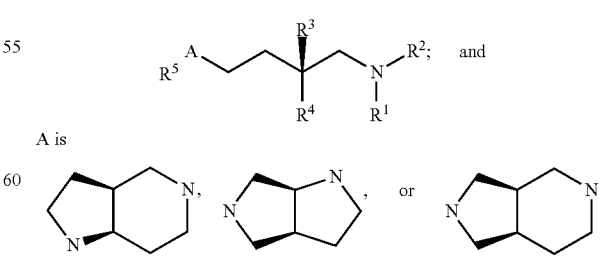

each of which is optionally substituted, is described. It is to be understood that the foregoing refer to both relative and absolute stereochemistry.

In another embodiment, herein described is the compound of any one of the preceding embodiments wherein the compound has the following stereochemistry

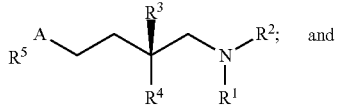

A is

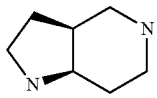

which is optionally substituted, is described. It is to be understood that the foregoing refers to both relative and absolute stereochemistry.

In another embodiment, the compound of any one of the preceding embodiments wherein A is

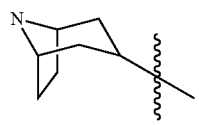 [SMILES: *C1CC2CCC(C1)N2]

which is optionally substituted. In one variation of the preceding embodiment, where $R^5$ is acylamino.

In another embodiment, the compound of any one of the preceding embodiments wherein A and $R^5$ are taken together to form one of the following

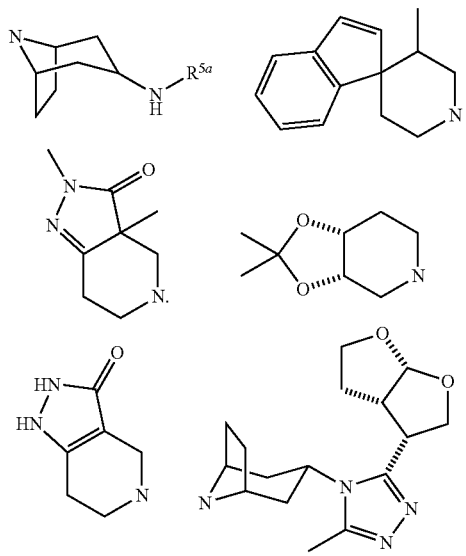

where $R^{5a}$ is hydrogen, acyl, or sulfonyl. In another embodiment, $R^{5a}$ and the attached nitrogen form a carbamate.

In another embodiment, the compound of any one of the preceding embodiments wherein A and $R^5$ are not taken together to form

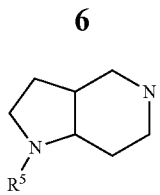

is described. In one variation, the compound of any one of the preceding embodiments wherein A and $R^5$ are not taken together to form

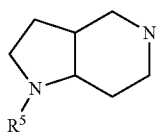

when $R^2$ is sulfonyl.

In another embodiment, the compound of any one of the preceding embodiments wherein A and $R^5$ are not taken together to form

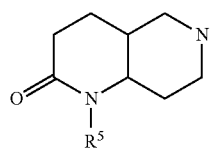

is described. In one variation, the compound of any one of the preceding embodiments wherein A and $R^5$ are not taken together to form

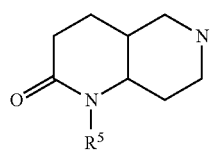

when $R^2$ is sulfonyl.

In another embodiment, the compound of any one of the preceding embodiments wherein $R^1$ is optionally substituted alkyl is described.

In another embodiment, the compound of any one of the preceding embodiments wherein $R^2$ is alkylsulfonyl or arylsulfonyl, each of which is optionally substituted is described.

In another embodiment, the compound of any one of the preceding embodiments wherein $R^2$ is optionally substituted arylsulfonyl is described.

In another embodiment, the compound of any one of the preceding embodiments wherein $R^2$ is optionally substituted arylsulfonyl and A is

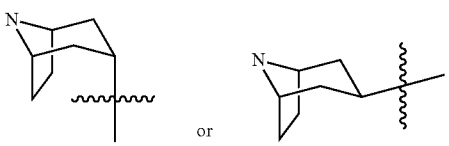 [SMILES: *C1CC2CCC(C1)N2 ; *C1CC2CCC(C1)N2]

is described. It is to be understood that the foregoing refer to both relative and absolute stereochemistry is described.

In another embodiment, the compound of any one of the preceding embodiments wherein R² is optionally substituted arylsulfonyl and A and R⁵ are taken together to form

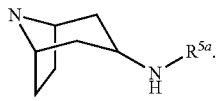

where R⁵ᵃ is hydrogen, acyl, or sulfonyl. In another embodiment, R⁵ᵃ and the attached nitrogen form a carbamate.

In another embodiment, the compound of any one of the preceding embodiments wherein R³ is hydrogen is described.

In another embodiment, the compound of any one of the preceding embodiments wherein R³ is optionally substituted alkyl is described.

In another embodiment, the compound of any one of the preceding embodiments wherein R³ is methyl is described.

In another embodiment, the compound of any one of the preceding embodiments wherein R⁴ is optionally substituted phenyl is described.

In another embodiment, the compound of any one of the preceding embodiments wherein R⁵ is H is described.

In another embodiment, the compound of any one of the preceding embodiments wherein R⁵ is acyl is described.

In another embodiment, the compound of any of the preceding embodiments wherein the conformationally constrained piperidine is a bridged bicycle.

In another embodiment, the compound of any one of the preceding embodiments wherein acyl is alkyloxycarbonyl, cycloalkyloxycarbonyl, heteroalkyloxycarbonyl, cycloheteroalkyloxycarbonyl, alkylaminocarbonyl, cycloalkylaminocarbonyl, heteroalkylaminocarbonyl, cycloheteroalkylaminocarbonyl, aryloxycarbonyl, arylalkyloxycarbonyl, arylaminocarbonyl, or arylalkylaminocarbonyl, each of which is optionally substituted is described.

In another embodiment, the compound of any one of the preceding embodiments wherein acyl in acylamino is alkyloxycarbonyl, cycloalkyloxycarbonyl, heteroalkyloxycarbonyl, cycloheteroalkyloxycarbonyl, alkylaminocarbonyl, cycloalkylaminocarbonyl, heteroalkylaminocarbonyl, cycloheteroalkylaminocarbonyl, aryloxycarbonyl, arylalkyloxycarbonyl, arylaminocarbonyl, or arylalkylaminocarbonyl, each of which is optionally substituted is described.

In another embodiment, the compound of any one of the preceding embodiments wherein R⁵ is alkylsulfonyl or arylsulfonyl, each of which is optionally substituted is described.

In another embodiment, the compound of any one of the preceding embodiments wherein R⁵ is optionally substituted heteroaryl is described.

In another embodiment, a pharmaceutical composition comprising one or more compounds of any one of the preceding embodiments is described.

In another embodiment, the composition of the preceding embodiment further comprising one or more carriers, diluents, or excipients, or a combination thereof is described.

In another embodiment, a method for treating a patient in need of relief from HIV infection, the method comprising the step of administering to the patient a therapeutically effective amount of the compound or the composition of any one of the preceding embodiments is described.

In another embodiment, use of the compound or composition of any one of the preceding embodiments in the manufacture of a medicament for the treatment of HIV infection is described.

In another embodiment, use of the compound or composition of any one of the preceding embodiments for the treatment of HIV infection is described.

It is to be understood that each of the foregoing embodiments may be combined in chemically relevant ways to generate subsets of the embodiments described herein. Accordingly, it is to be further understood that all such subsets are also illustrative embodiments of the invention described herein. For example, in another embodiment, the compound wherein R⁵ is acyl, where acyl is arylalkyloxycarbonyl, R⁴ is optionally substituted phenyl, and R² is optionally substituted arylsulfonyl is described.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

As used herein, the term "alkyl" includes a chain of carbon atoms, which is optionally branched. It is to be understood that alkyl is advantageously of limited length, including $C_1$-$C_{24}$, $C_1$-$C_{12}$, $C_1$-$C_8$, $C_1$-$C_6$, and $C_1$-$C_4$. It is appreciated herein that shorter alkyl groups add less lipophilicity to the compound and accordingly will have different pharmacokinetic behavior. As used herein, the term "cycloalkyl" includes a chain of carbon atoms, which is optionally branched, and where at least a portion of the chain in cyclic. It is to be understood that chain forming cycloalkyl is advantageously of limited length, including $C_3$-$C_{24}$, $C_3$-$C_{12}$, $C_3$-$C_8$, $C_3$-$C_6$, and $C_3$-$C_4$. It is appreciated herein that shorter alkyl groups add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "heterocyclyl" including heterocycle includes a chain of atoms that includes both carbon and at least one heteroatom, and is optionally branched, where at least a portion of the chain is cyclic. Illustrative heteroatoms include nitrogen, oxygen, and sulfur. In certain variations, illustrative heteroatoms also include phosphorus, and selenium. Illustrative heteocycles include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, alkyloxycarbonyl, cycloalkyloxycarbonyl, heteroalkyloxycarbonyl, cycloheteroalkyloxycarbonyl, alkylaminocarbonyl, cycloalkylaminocarbonyl, heteroalkylaminocarbonyl, cycloheteroalkylaminocarbonyl, aryloxycarbonyl, arylalkyloxycarbonyl, arylaminocarbonyl, arylalkylaminocarbonyl, and the like, each of which is optionally substituted.

As used herein, the term "aryl" includes monocyclic and polycyclic aromatic carbocyclic and aromatic heterocyclic groups, each of which may be optionally substituted. As used herein, the term "heteroaryl" includes aromatic heterocyclic groups, each of which may be optionally substituted. Illustrative carbocyclic aromatic groups described herein include, but are not limited to, phenyl, naphthyl, and the like. Illustrative heterocyclic aromatic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "optionally substituted amino" includes derivatives of amino as described herein, such as, but not limited to, acylamino, urea, and carbamate, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

The term "optionally substituted aryl" as used herein includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

Illustrative substituents include, but are not limited to, a radical —$(CH_2)_mZ$, where m is an integer from 0-6 and Z is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or Z is selected from —$CO_2R^4$ and —$CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl)pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$) alkoxy, each of which is optionally further substituted with one or more of 1 to 3 halogen atoms; optionally substituted aryl($C_2$-$C_{16}$)alkanoyl, such as the aryl radical being unsubstituted or substituted by 1 to 3 substituents selected from the group consisting of halogen, ($C_1$-$C_3$)alkyl and ($C_1$-$C_3$) alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known in the medical arts.

It is also appreciated that the therapeutically effective amount is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a co-therapy.

The compounds described herein can be prepared and administered in a wide variety of conventional oral, parenteral, and topical dosage forms, utilizing art-recognized products. See generally, Remington: The Science and Practice of Pharmacy, ($21^{st}$ ed., 2005). Thus, the compounds described herein can be administered by injection (e.g. intravenously, intramuscularly, intracutaneously, subcutaneously, intraduodenally, or intraperitoneally). Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds described herein. It is also to be understood that the compositions may be prepared from various amorphous, non-amorphous, partially crystalline, crystalline, and/or other morphological forms of the compounds described herein.

The term "administering" as used herein includes systemic use, as when taken orally, parenterally (including by subcutaneous, intramuscular, intravenous and intraarterial routes), or topically in dosage form unit formulations containing conventional nontoxic pharmaceutically-acceptable carriers, adjuvants and vehicles. Suitable routes for parenteral administration include intravenous, intraarterial, intraperitoneal, epidurial, intraurethral, intrasternal, intramuscular and subcutaneous, as well as any other art recognized route of parenteral administration. Suitable means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art. The term "administering" as used herein also includes local use, as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also contemplated herein.

Depending upon the disease as described herein, the route of administration and/or whether the compounds and/or compositions are administered locally or systemically, a wide range of permissible dosages are contemplated herein, including doses falling in the range from about 1 µg/kg to about 1 g/kg. The dosages may be single or divided, and may administered according to a wide variety of protocols, including q.d., b.i.d., t.i.d., or even every other day, once a week, once a month, once a quarter, and the like. In each of these cases it is understood that the total daily, weekly, month, or quarterly dose corresponds to the therapeutically effective amounts described herein. When given systemically, such as parenterally, illustrative doses include those in the range from about 0.01 mg/kg to about 100 mg/kg, or about 0.01 mg/kg to about 10 mg/kg, or about 0.1 mg/kg to about 100 mg/kg, or about 0.1 mg/kg to about 10 mg/kg. When given systemically, such as orally, illustrative doses include those in the range from about 0.1 mg/kg to about 1000 mg/kg, or about 0.1 mg/kg to about 100 mg/kg, or about 0.1 mg/kg to about 10 mg/kg, or about 1 mg/kg to about 1000 mg/kg, or about 1 mg/kg to about 100 mg/kg, or about 1 mg/kg to about 10 mg/kg.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, ointments, soft and hard gelatin capsules, sterile injectable solutions, and sterile packaged powders. The compositions may contain anywhere from about 0.1% to about 99.9% active ingredients, depending upon the selected dose and dosage form. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (Generally Regarded as Safe) compounds.

Solid Dosage Forms for Oral Use. Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Controlled Release Oral Dosage Forms. Controlled release compositions for oral use may, e.g., be constructed to release the active drug by controlling the dissolution and/or the diffusion of the active drug substance. Illustrative sustained release formulations are described in U.S. Pat. Nos. 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are incorporated herein by reference.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration. Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monoleate, polyoxyethylene sorbitan monoleate, and the like). Suitable suspending agents are, for example, sodium carboxymethylcellulose, methylcellulose, sodium alginate, and the like.

Parenteral Compositions. The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions described herein may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions. Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters)).

Percutaneous and Topical Compositions. The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

Examples of emulsifying agents are naturally occurring gums (e.g., gum acacia or gum tragacanth) and naturally occurring phosphatides (e.g., soybean lecithin and sorbitan monoleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monoleate (TWEEN)).

The pharmaceutical compositions described above for topical administration on the skin may also be used in connection with topical administration onto or close to the part of the body that is to be treated. The compositions may be adapted for direct application or for introduction into relevant orifice(s) of the body (e.g., rectal, urethral, vaginal or oral orifices). The composition may be applied by means of special drug delivery devices such as dressings or alternatively plasters, pads, sponges, strips, or other forms of suitable flexible material.

Controlled Release Percutaneous and Topical Compositions. There are several approaches for providing rate control over the release and transdermal permeation of a drug, including: membrane-moderated systems, adhesive diffusion-controlled systems, matrix dispersion-type systems, and microreservoir systems. A controlled release percutaneous and/or topical composition may be obtained by using a suitable mixture of the above-mentioned approaches.

In a membrane-moderated system, the active drug is present in a reservoir which is totally encapsulated in a shallow compartment molded from a drug-impermeable laminate, such as a metallic plastic laminate, and a rate-controlling polymeric membrane such as a microporous or a non-porous polymeric membrane (e.g., ethylene-vinyl acetate copolymer). The active compound is only released through the rate-controlling polymeric membrane. In the drug reservoir, the active drug substance may either be dispersed in a solid polymer matrix or suspended in a viscous liquid medium such as silicone fluid. On the external surface of the polymeric membrane, a thin layer of an adhesive polymer is applied to achieve an intimate contact of the transdermal system with the skin surface. The adhesive polymer is preferably a hypoallergenic polymer that is compatible with the active drug.

In an adhesive diffusion-controlled system, a reservoir of the active drug is formed by directly dispersing the active drug in an adhesive polymer and then spreading the adhesive containing the active drug onto a flat sheet of substantially drug-impermeable metallic plastic backing to form a thin drug reservoir layer. A matrix dispersion-type system is characterized in that a reservoir of the active drug substance is formed by substantially homogeneously dispersing the active drug substance in a hydrophilic or lipophilic polymer matrix and then molding the drug-containing polymer into a disc with a substantially well-defined surface area and thickness. The adhesive polymer is spread along the circumference to form a strip of adhesive around the disc.

In a microreservoir system, the reservoir of the active substance is formed by first suspending the drug solids in an aqueous solution of water-soluble polymer, and then dispersing the drug suspension in a lipophilic polymer to form a plurality of microscopic spheres of drug reservoirs.

Dosages. The dosage of each compound of the claimed combinations depends on several factors, including: the administration method, the severity of disease, whether the disease is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

As described above, the compound in question may be administered orally in the form of tablets, capsules, elixirs or syrups. Parenteral administration of a compound is suitably performed, for example, in the form of saline solutions or with the compound incorporated into liposomes. In cases where the compound in itself is not sufficiently soluble to be dissolved, a solubilizer such as ethanol can be applied.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

EXAMPLES

The compounds described herein can be prepared from commercially available materials using methods well-known to a person having ordinary skill in the art of organic synthesis. Illustrative methods are shown in the following examples.

Synthesis of Example 1 and 2 a) Synthesis of the quaternary chiral aldehyde:

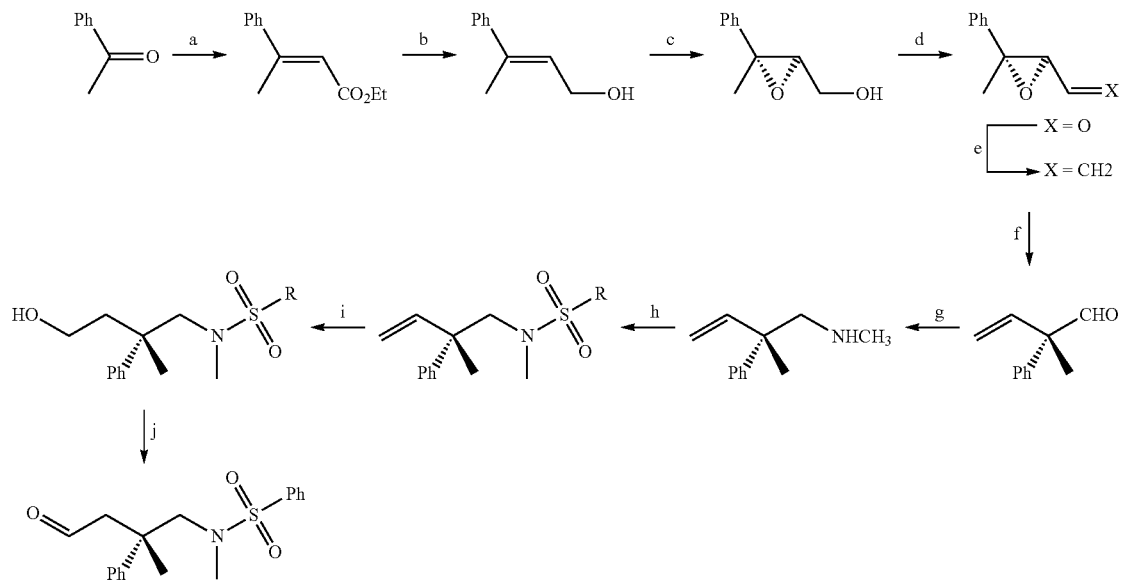

Conditions: a) NaH, THF; EtO$_2$CCH$_2$P(O)(OEt)$_2$, reflux. b) DIBA1-H, DCM, 0° C. c) Ti(i-PrO)$_4$, DET, TBHP, DCM, MS 4 A, -20° C., d) (COCl)$_2$, DMSO, Et$_3$N, DCM, -78° C. e) NaHMDS, Ph$_3$P(CH$_3$)Br. f) BF$_3$·Et$_2$O, DCM, -78° C. g) MeNH$_2$, NaBH(OAc)$_3$, DCE. h) PhSO$_2$Cl, Et$_3$N, DCM. i) BH$_3$·THF; H$_2$O$_2$, pH7 buffer. j) (COCl)$_2$, DMSO, Et$_3$N, DCM. -78° C.

b) Synthesis of the chiral bicyclic heterocycle

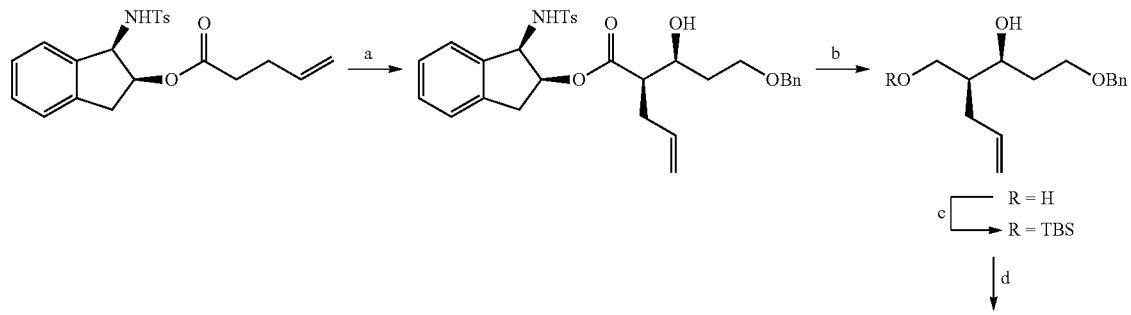

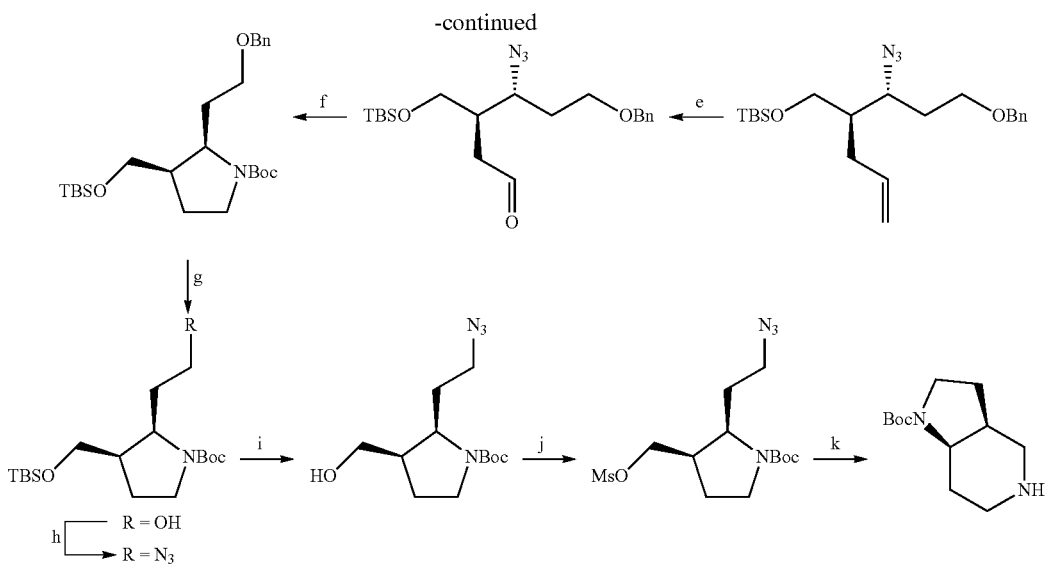

Conditions: a) TiCl₄, i-Pr₂EtN, DCM; BnO(CH₂)₂CHO. b) LiAlH₄, THF. c) TBSCl, i-Pr₂EtN, DMF, 0° C., d) DIAD, Ph₃P, HN₃, PhMe, 0° C. to rt. e)cat OsO₄, NMO; NaIO₄, aq THF. f) H₂, Pd—C,MeOH; NaBH(OAc)₃; Et₃N, Boc₂O. g) H₂,Pd—C, MeOH. h) DIAD, Ph₃P, HN₃, PhMe. i) TBAF, THF. j) MsCl, Et₃N, DCM, 0° C. k) H₂,Pd—C, MeOH, rt, then reflux.

c) Coupling of two fragments:

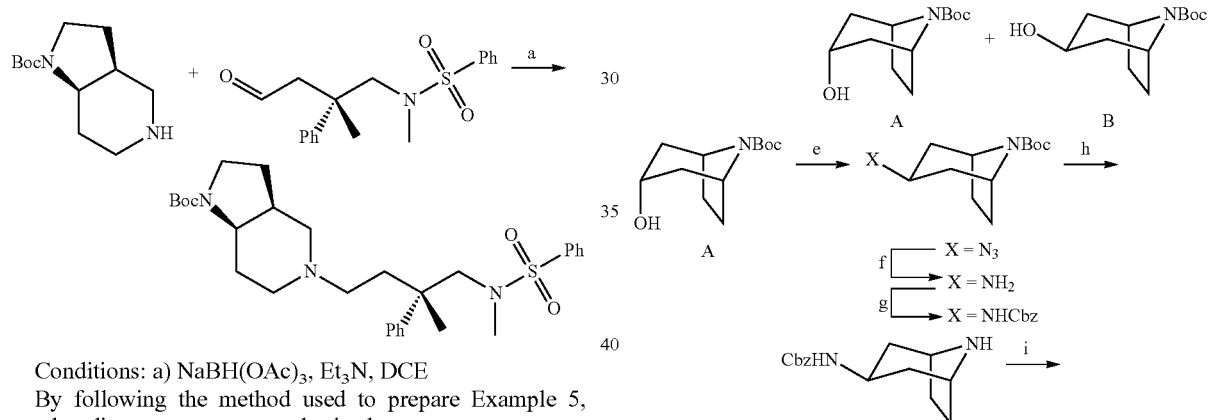

Conditions: a) NaBH(OAc)₃, Et₃N, DCE

By following the method used to prepare Example 5, another diastereomer was synthesized:

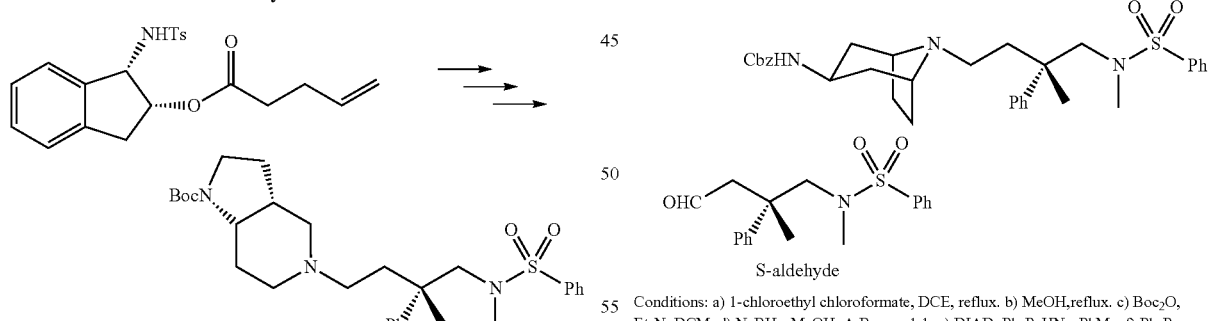

Synthesis of Example 5 and 6 a) Synthesis of the

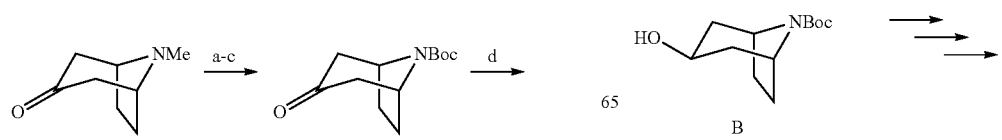

Similarly, Example 6 was synthesized from the equatorial alcohol:

Conditions: a) 1-chloroethyl chloroformate, DCE, reflux. b) MeOH,reflux. c) Boc₂O, Et₃N, DCM. d) NaBH₄, MeOH, A:B = ca. 1:1. e) DIAD, Ph₃P, HN₃, PhMe. f) Ph₃P, MeOH. g) CbzCl, Na₂CO₃, aq THF. h) TFA, DCM. i) S-aldehyde, NaBH(OAc)₃, Et₃N, DCE.

-continued

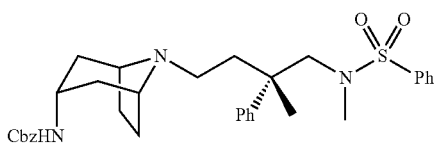

Synthesis of 3

Example 24

To a solution of amine 1 (43 mg, 0.19 mmol) in DCM (2 mL), aldehyde 2 (53 mg, 0.16 mmol), AcOH (29 µL) and Na(OAc)₃BH (51 mg, 0.24 mmol) were added successively at 23° C. under argon and the resulting mixture was stirred for 12 h at the same temperature. The reaction mixture was neutralized with 2N NaOH and diluted with DCM. Organic layer was separated and the aqueous layer was extracted with DCM. The combined organic layers were washed with brine and dried over anhydrous Na₂SO₄. Solvent was removed under reduced pressure and the resulting residue was purified by column chromatography over silica gel (2% MeOH/EtOAc) to provide BOC-derivative 3 (Example 24) (Yield: 70 mg, 81%, solid). ¹HNMR (400 MHz, CDCl₃): δ1.33-1.44 (br, 11H), 1.50 (s, 3H), 1.52-1.63 (m, 2H), 1.72-1.89 (m, 4H), 1.89-2.21 (m, 6H), 2.22-2.37 (m, 1H), 2.90 (d, 1H, J=13.7 Hz), 3.09-3.31 (br, 2H), 3.43 (d, 1H, J=13.7 Hz), 3.66-3.88 (br, 1H), 4.14-4.39 (br, 1H), 7.16-7.22 (m, 1H), 7.27-7.38 (m, 4H), 7.46-7.53 (m, 2H), 7.53-7.61 (m, 1H), 7.64-7.79 (m, 2H).

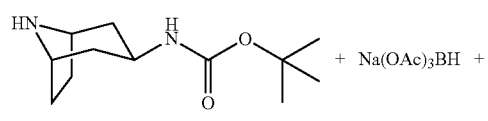

Synthesis of 4

To a suspension of NaH (20.8 mg 60% NaH, 0.52 mmol) in dry THF (1 mL), BOC-derivative 3 (28.2 mg, 0.052 mmol, in 1 mL THF) was added at 0° C. and the resulting mixture was stirred at 0° C. for 15 min. Allyl bromide (45 µL, 0.52 mmol) was added to the reaction mixture at the same temperature. The mixture was refluxed for 3 h. The reaction was cooled to 0° C. and was quenched by addition of water carefully. The reaction mixture was extracted with ethyl acetate and dried over anhydrous Na₂SO₄. The solvent was removed under reduced pressure and the resulting residue was purified by column chromatography over silica gel to provide 4 (2% (5% NH₃/MeOH)/CHCl₃). (Yield: 12.1 mg, 40%, colorless oil). ¹HNMR (400 MHz, CDCl₃): δ1.24-1.48 (br, 11H), 1.51 (s, 3H), 1.59-1.98 (br, 7H), 2.01-2.25 (br, 5H), 2.28-2.50 (br, 1H), 2.90 (d, 1H, J=13.7 Hz), 3.09-3.40 (br, 2H), 3.42 (d, 1H, J=13.7 Hz), 3.51-3.78 (br, 2H), 4.08-4.48 (br, 1H), 4.98-5.19 (m, 2H), 5.64-5.82 (br, 1H), 7.16-7.22 (m, 1H), 7.26-7.42 (m, 4H), 7.43-7.64 (m, 3H), 7.68-7.82 (m, 2H).

Synthesis of 6

To the solution of 4 (9.9 mg, 0.017 mmol) in DCM (1 mL), trifluoroacetic acid (0.1 mL) was added at 0° C. and the resulting mixture was stirred for 1 h at 23° C. The reaction mixture was diluted with DCM and neutralized by the slow addition of saturated NaHCO₃ solution. The layers were separated and the aqueous layer was extracted with DCM. The combined organic layers were washed with brine and dried over anhydrous Na₂SO₄. The solvent was removed under reduced pressure and the resulting compound 5 was used in the next step without further purification.

To the solution of the above crude compound 5 in DCM (1 mL), Et₃N (24 µL, 0.17 mmol) and 4-nitrobenzyl chloroformate (18.3 mg, 0.085 mmol) were added successively at 0° C. The resulting mixture was stirred for 1 h at 23° C. After this period, the reaction was quenched by addition of water and extracted with DCM several times. The combined organic layers were washed with brine and dried over anhydrous Na₂SO₄. The solvent was removed under reduced pressure and the resulting residue was purified by column chromatography over silica gel (2% (5% NH₃/MeOH)/CHCl₃) to provide inhibitor 6 (Yield: 6.3 mg, 56%, colorless oil). ¹HNMR (400 MHz, CDCl₃): δ1.37-1.48 (br, 2H), 1.51 (s, 3H), 1.52-1.62 (br, 2H), 1.71-1.93 (m, 4H), 1.97-2.18 (m, 5H), 2.22-2.42 (br, 1H), 2.84-2.98 (m, 1H), 3.13-3.37 (br, 2H), 3.42 (d, 1H, J=13.7 Hz), 3.60-3.92 (m, 2H), 4.01-4.48 (br, 1H), 4.98-5.30 (m, 4H), 5.64-5.82 (m, 1H), 7.17-7.24 (m, 1H), 7.27-7.38 (m, 4H), 7.42-7.61 (m, 5H), 7.69-7.82 (m, 2H), 8.20 (d, 2H, J=8.0 Hz).

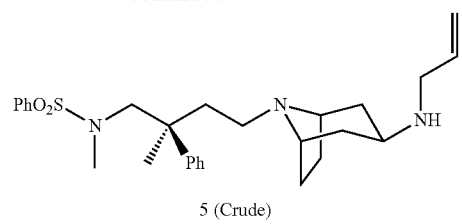

5 (Crude)

DCM
0-23° C., 1 h
56%

Et₃N

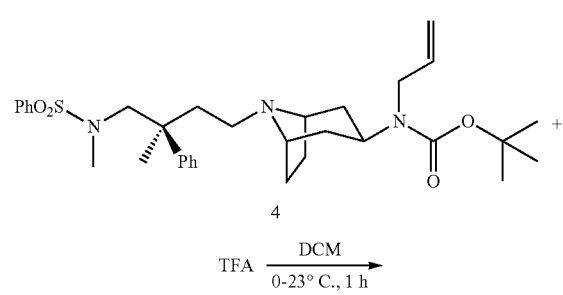

4

TFA $\xrightarrow[\text{0-23° C., 1 h}]{\text{DCM}}$ +

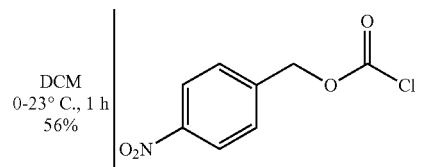

6

| Inhibition Data | |
|---|---|
| Structure | Activity (*) |
| 1 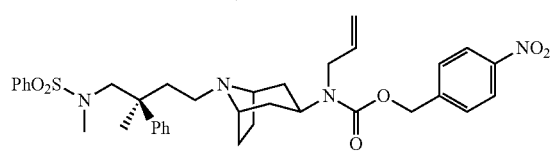 | ++++ |
| 2 | + |
| 3 | + |

-continued

| | Inhibition Data | |
|---|---|---|
| | Structure | Activity (*) |
| 4 | [structure] | ++++ |
| 5 | [structure] | ++ |
| 6 | [structure] | ++ |
| 7 | [structure] | ++ |
| 8 | [structure] | + |
| 9 | [structure] | ++ |

-continued

| | Inhibition Data | |
|---|---|---|
| | Structure | Activity (*) |
| 10 | | ++ |
| 11 | | ++ |
| 12 | | ++ |
| 13 | | ++ |
| 14 | | + |

-continued
| | Inhibition Data | |
|---|---|---|
| | Structure | Activity (*) |
| 15 | 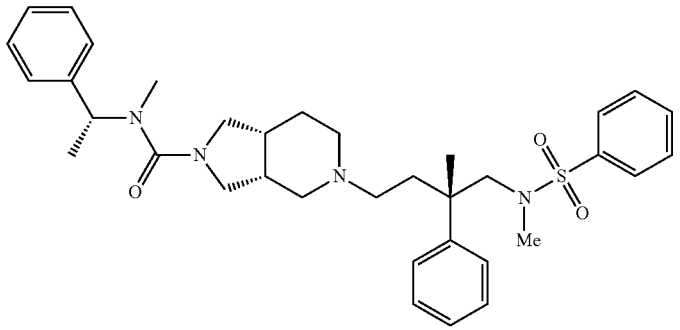 [SMILES: C[C@H](c1ccccc1)N(C)C(=O)N1C[C@H]2CN(CC[C@](C)(CN(C)S(=O)(=O)c3ccccc3)c3ccccc3)CC[C@H]2C1] | ++ |
| 16 | 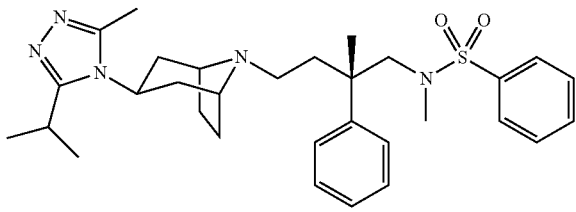 [SMILES: Cc1nnc(C(C)C)n1C1CC2CCC(C1)N2CC[C@](C)(CN(C)S(=O)(=O)c1ccccc1)c1ccccc1] | +++ |
| 17 | 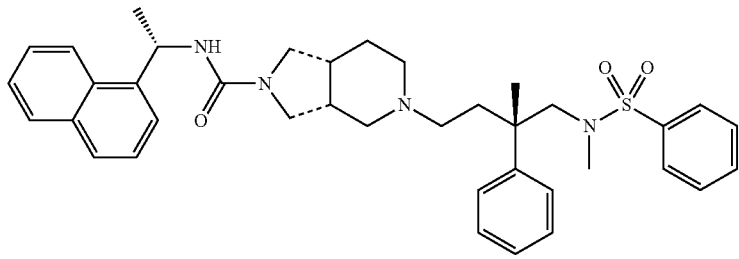 | + |
| 18 | 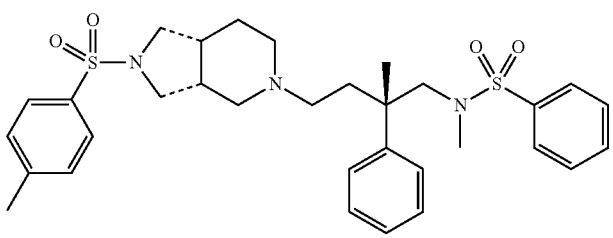 | + |
| 19 | 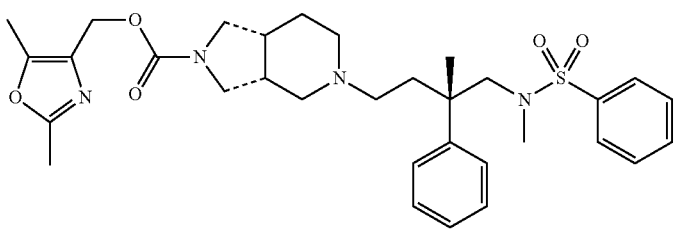 | + |
| 20 | 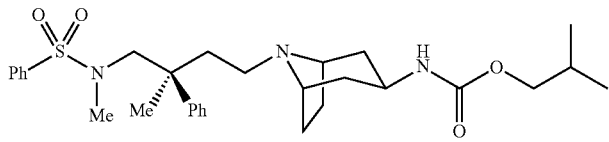 [SMILES: CC(C)COC(=O)NC1CC2CCC(C1)N2CC[C@](C)(CN(C)S(=O)(=O)c1ccccc1)c1ccccc1] | ++ |

-continued

| | Inhibition Data | |
|---|---|---|
| | Structure | Activity (*) |
| 21 | | ++ |
| 22 | | + |
| 23 | | NT |
| 24 | | NT |
| 25 | | +++ |
| 26 | | + |
| 27 | | + |

-continued

| | Inhibition Data | |
|---|---|---|
| | Structure | Activity (*) |
| 28 | [structure: hexahydrofuro[3,2-b]furan-3-yl ester of octahydropyrrolo[3,2-c]pyridine-1-carboxylate, with N-linked CH₂CH₂C(Me)(Ph)CH₂N(Me)S(O)₂Ph side chain] | ++ |
| 29 | [structure: (tetrahydrofuran-3-yl) ester of octahydropyrrolo[3,2-c]pyridine-1-carboxylate, with N-linked CH₂CH₂C(Me)(Ph)CH₂N(Me)S(O)₂Ph side chain] | + |
| 30 | [structure: BocN-octahydropyrrolo[3,2-c]pyridine with N-linked CH₂CH₂C(OMe)(Ph)CH₂N(Me)S(O)₂Ph side chain] | + |
| 31 | [structure: BocN-octahydropyrrolo[3,2-c]pyridine with N-linked CH₂CH₂C(OMe)(Ph)CH₂N(Me)S(O)₂Ph side chain, opposite stereochem] | + |
| 32 | [structure: BocN-octahydropyrrolo[3,2-c]pyridine with N-linked CH₂CH₂C(Me)(Ph)CH₂N(Me)S(O)₂Ph side chain] from enantiomerically enriched (−)-acid (4:1) | ++ |
| 33 | [structure: BocN-octahydropyrrolo[3,2-c]pyridine with N-linked CH₂CH₂C(Me)(Ph)CH₂N(Me)S(O)₂-C₆H₄-C(O)OCH₂Ph side chain] | + |

-continued

| | Inhibition Data | |
|---|---|---|
| | Structure | Activity (*) |
| 34 | (structure) | ++ |
| 35 | (structure) | ++ |
| 36 | (structure) | ++ |
| 37 | (structure) | + |
| 38 | (structure) | ++ |

-continued

| | Inhibition Data | |
|---|---|---|
| | Structure | Activity (*) |
| 39 | *[structure: Boc-pyrrolidine-fused piperidine-N-CH2-C(Me)(Ph)-CH2-N(Me)-SO2-C6H4-CH2-NH-C(=O)-O-tBu]* | + |
| 40 | *[structure: Boc-pyrrolidine-fused piperidine-N-CH2-C(Me)(Ph)-CH2-N(Me)-SO2-C6H4-CH2-NH-C(=O)-O-(tetrahydrofuran-3-yl)]* | ++ |
| 41 | *[structure: Boc-pyrrolidine-fused piperidine-N-CH2-C(Me)(Ph)-CH2-N(Me)-SO2-C6H4-CH2-NH2]* | + |
| 42 | *[structure: cis-Boc-octahydropyrrolo[3,2-c]pyridine-N-CH2-C(Me)(Ph)-CH2-N(Me)-SO2-Ph, with stereochemistry]* | + |
| 43 | *[structure: Boc-octahydropyrrolo[3,2-c]pyridine-N-CH2-C(Me)(Ph)-CH2-N(Me)-SO2-Ph, stereoisomer]* | ++ |
| 44 | *[structure: Boc-octahydropyrrolo[3,2-c]pyridine-N-CH2-C(Me)(Ph)-CH2-N(Me)-SO2-Ph, stereoisomer]* | +++ |

-continued

| | Inhibition Data | |
|---|---|---|
| | Structure | Activity (*) |
| 45 | *(structure)* | + |
| 46 | *(structure)* | + |
| 47 | *(structure)* | + |
| 48 | *(structure)* | + |
| 49 | *(structure)* | ++ |

-continued
| | Inhibition Data | |
|---|---|---|
| | Structure | Activity (*) |
| 50 | 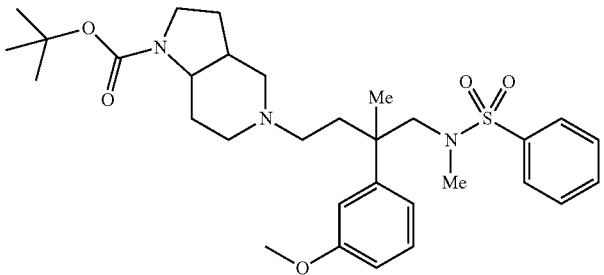 [SMILES: COc1cccc(C(C)(CCN2CCC3C(CCN3C(=O)OC(C)(C)C)C2)CN(C)S(=O)(=O)c2ccccc2)c1] | + |
| 51 | 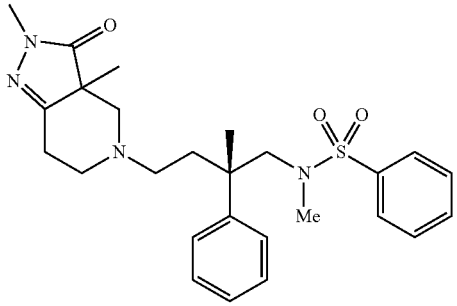 [SMILES: CN1N=C2CCN(CC[C@](C)(CN(C)S(=O)(=O)c3ccccc3)c3ccccc3)CC2(C)C1=O] | + |
| 52 | 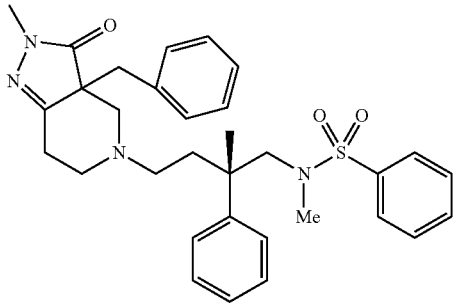 [SMILES: CN1N=C2CCN(CC[C@](C)(CN(C)S(=O)(=O)c3ccccc3)c3ccccc3)CC2(Cc2ccccc2)C1=O] | + |
| 56 | 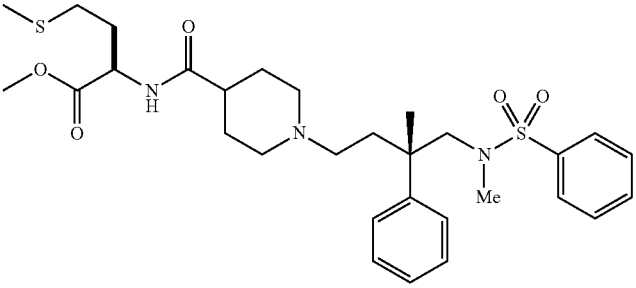 [SMILES: COC(=O)[C@@H](CCSC)NC(=O)C1CCN(CC[C@](C)(CN(C)S(=O)(=O)c2ccccc2)c2ccccc2)CC1] | + |
| 58 | 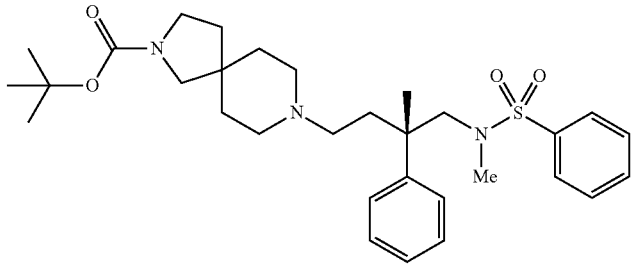 [SMILES: CN(C[C@@](C)(CCN1CCC2(CC1)CCN(C(=O)OC(C)(C)C)C2)c1ccccc1)S(=O)(=O)c1ccccc1] | + |

-continued

Inhibition Data

| | Structure | Activity (*) |
|---|---|---|
| 64 | 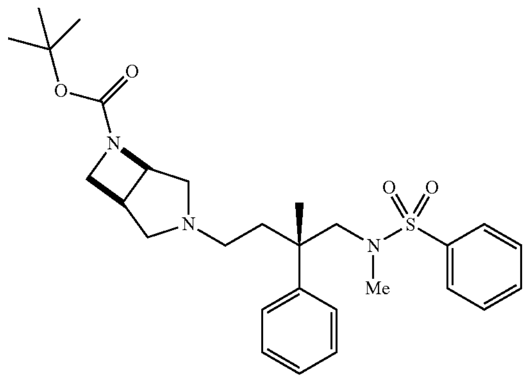 | + |
| 65 | 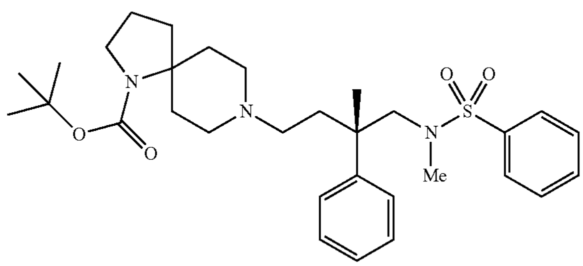 [SMILES: CN(C[C@@](C)(CCN1CCC2(CCCN2C(=O)OC(C)(C)C)CC1)c1ccccc1)S(=O)(=O)c1ccccc1] | + |
| 66 | 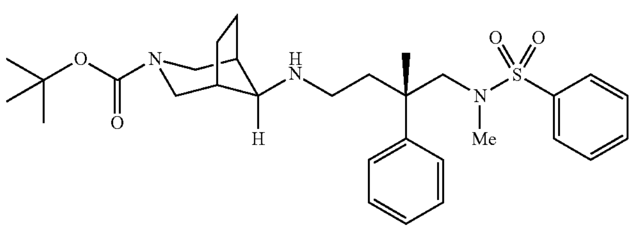 [SMILES: CN(C[C@@](C)(CCNC1C2CCC1CN(C(=O)OC(C)(C)C)C2)c1ccccc1)S(=O)(=O)c1ccccc1] | + |
| 67 | 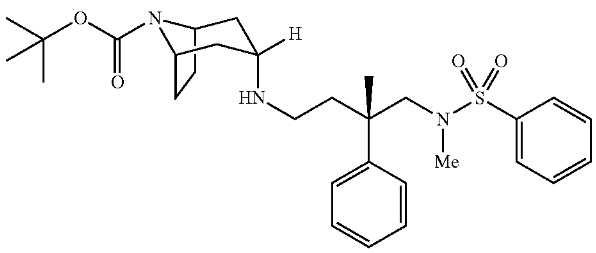 [SMILES: CN(C[C@@](C)(CCNC1CC2CCC(C1)N2C(=O)OC(C)(C)C)c1ccccc1)S(=O)(=O)c1ccccc1] | + |
| 69 | 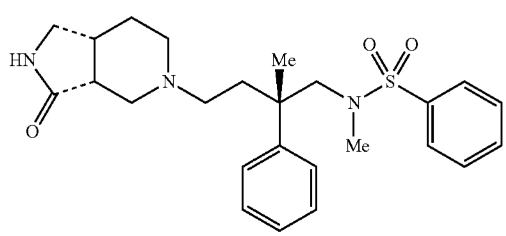 | + |

Inhibition Data

| | Structure | Activity (*) |
|---|---|---|
| 70 | 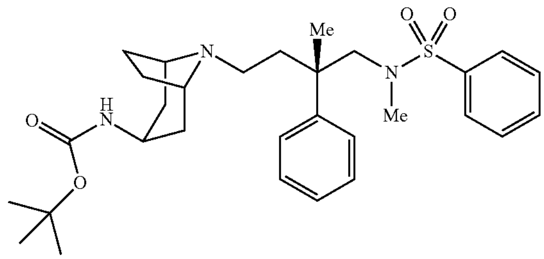 [SMILES: CN(C[C@@](C)(CCN1C2CCC1CC(NC(=O)OC(C)(C)C)C2)c1ccccc1)S(=O)(=O)c1ccccc1] | + |
| 71 | 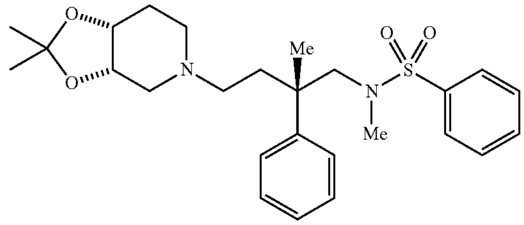 | + |
| 72 | 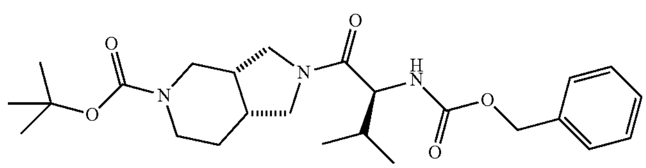 | + |
| 74 | 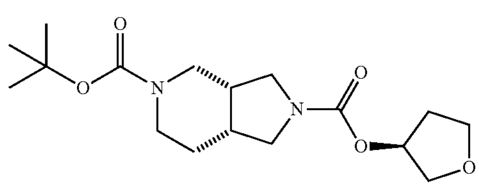 | + |
| 75 | (more polar) | + |
| 76 | 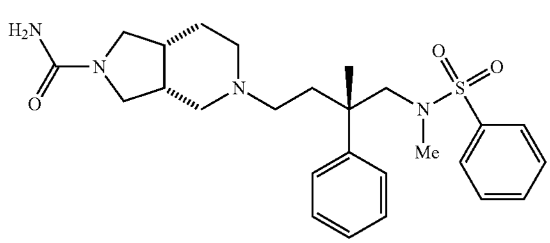 | + |

-continued

| | Inhibition Data | |
|---|---|---|
| | Structure | Activity (*) |
| 78 | | + |
| 79 | | + |
| 80 | | ++ |
| 81 | | + |
| 82 | | + |

-continued

Inhibition Data

| Structure | Activity (*) |
|---|---|
| 83 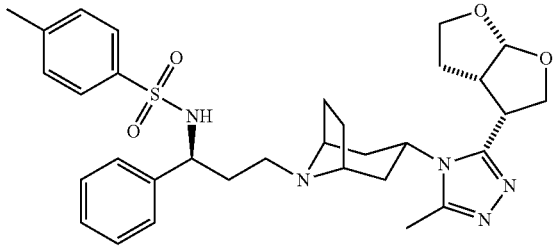 | + |

(*) +, IC$_{50}$ < 1000 nM; ++, IC$_{50}$ < 100 nM; +++, IC$_{50}$ < 10 nM; and ++++, IC$_{50}$ < 1 nM

What is claimed is:

1. A compound of the formula:

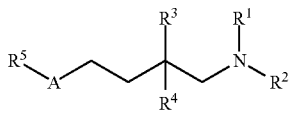

or a pharmaceutically acceptable salt thereof, wherein:
A is

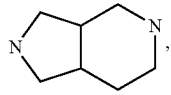

R$^1$ is hydrogen or optionally substituted alkyl;
R$^2$ is alkylsulfonyl or arylsulfonyl, each of which is optionally substituted;
R$^3$ is hydrogen or optionally substituted alkyl;
R$^4$ is optionally substituted aryl; and
R$^5$ is acyl, acylamino, sulfonyl, or sulfonylamino;
wherein acyl or acyl in acylamino is alkyloxycarbonyl, cycloalkyloxycarbonyl, heteroalkyloxycarbonyl, cycloheteroalkyloxycarbonyl, alkylaminocarbonyl, cycloalkylaminocarbonyl, heteroalkylaminocarbonyl, cycloheteroalkylaminocarbonyl, aryloxycarbonyl, arylalkyloxycarbonyl, arylaminocarbonyl or arylalkylaminocarbonyl, each of which is optionally substituted;
or A is:

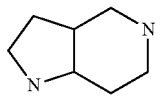

R$^1$ is hydrogen or optionally substituted alkyl;
R$^2$ is alkylsulfonyl or arylsulfonyl, wherein the alkyl in alkyl sulfonyl is optionally substituted and the aryl in arylsulfonyl is substituted;
R$^3$ is hydrogen or optionally substituted alkyl;
R$^4$ is optionally substituted aryl; and
R$^5$ is acyl, acylamino, sulfonyl, or sulfonylamino;
wherein acyl or acyl in acylamino is alkyloxycarbonyl, cycloalkyloxycarbonyl, heteroalkyloxycarbonyl, cycloheteroalkyloxycarbonyl, alkylaminocarbonyl, cycloalkylaminocarbonyl, heteroalkylaminocarbonyl, cycloheteroalkylaminocarbonyl, aryloxycarbonyl, arylalkyloxycarbonyl, arylaminocarbonyl or arylalkylaminocarbonyl, each of which is optionally substituted.

2. The compound or salt of claim 1 wherein the compound has the following absolute stereochemistry

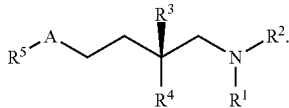

3. The compound or salt of claim 1 wherein A is

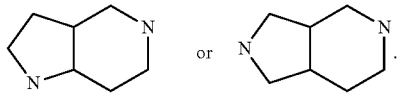 [SMILES: C1CC2NCCC2CN1 ; C1CC2CNCC2CN1]

4. The compound or salt of claim 1 wherein A is

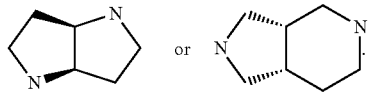 [SMILES: C1C[C@H]2NCC[C@H]2N1 ; C1C[C@@H]2CNC[C@@H]2CN1]

5. The compound or salt of claim 1 wherein R$^1$ is optionally substituted alkyl.

6. The compound or salt of claim 1 wherein when A is:

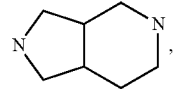

R$^2$ is optionally substituted arylsulfonyl.

7. The compound or salt of claim 1 wherein R$^3$ is methyl.

8. The compound or salt of claim 1 wherein R$^4$ is optionally substituted phenyl.

9. The compound or salt of claim 1 wherein R$^5$ is acyl.

10. The compound or salt of claim 1 wherein R$^5$ is alkylsulfonyl or arylsulfonyl, each of which is optionally substituted.

11. A pharmaceutical composition comprising one or more compounds of claim 1 or a pharmaceutically acceptable salt thereof and further comprising one or more carriers, diluents, or excipients, or a combination thereof.

12. A method for treating a patient in need of relief from HIV infection, the method comprising the step of administering to the patient a therapeutically effective amount of the compound of claim 1, or a pharmaceutically acceptable salt thereof.

13. The compound or salt of claim 1 wherein the compound is:

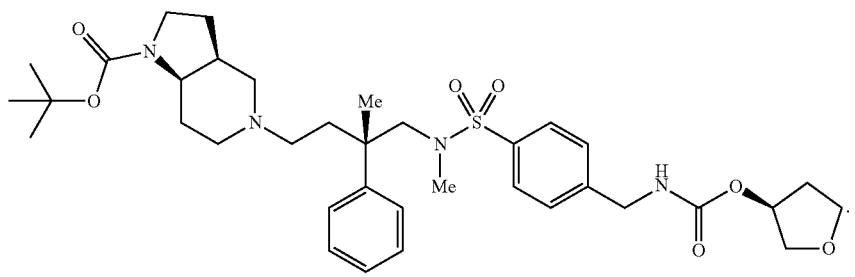 [SMILES: CN(C[C@@](C)(CCN1CC[C@@H]2[C@@H](CCN2C(=O)OC(C)(C)C)C1)c1ccccc1)S(=O)(=O)c1ccc(CNC(=O)O[C@H]2CCOC2)cc1]
* * * * *